United States Patent
Scimone et al.

(10) Patent No.: US 10,524,828 B2
(45) Date of Patent: Jan. 7, 2020

(54) CUTTING DEVICE

(71) Applicant: Slice, Inc., San Jose, CA (US)

(72) Inventors: Thomas Scimone, Campbell, CA (US); Scot Herbst, Santa Cruz, CA (US); William W Hunter, Santa Cruz, CA (US); Robert Joseph Gallegos, Fremont, CA (US)

(73) Assignee: Slice, Inc., San Jose, CA (US)

( * ) Notice: Subject to any disclaimer, the term of this patent is extended or adjusted under 35 U.S.C. 154(b) by 0 days.

(21) Appl. No.: 15/944,036

(22) Filed: Apr. 3, 2018

(65) Prior Publication Data
US 2018/0289386 A1    Oct. 11, 2018

Related U.S. Application Data

(60) Provisional application No. 62/482,569, filed on Apr. 6, 2017.

(51) Int. Cl.
*A61B 17/3213* (2006.01)
*B25G 3/10* (2006.01)
*F16F 1/18* (2006.01)
*A61B 17/3211* (2006.01)

(52) U.S. Cl.
CPC ............ *A61B 17/3213* (2013.01); *B25G 3/10* (2013.01); *A61B 2017/32113* (2013.01); *F16F 1/18* (2013.01)

(58) Field of Classification Search
CPC .................................. B25G 3/10; B25G 3/28
USPC ............................ 30/335, 342, 162, 322–328
See application file for complete search history.

(56) References Cited

U.S. PATENT DOCUMENTS

| | | | | |
|---|---|---|---|---|
| 1,636,062 A * | 7/1927 | Maclure | ............ | A61B 17/3213 279/9.1 |
| 1,887,188 A * | 11/1932 | Ross | ................ | B26B 5/006 30/162 |
| 2,291,514 A * | 7/1942 | Warner | ............... | B44D 3/162 30/162 |
| 2,736,964 A * | 3/1956 | Lieberman | ......... | A61B 17/3211 30/336 |
| 2,960,769 A * | 11/1960 | Matwijcow | ......... | A61B 17/3213 30/339 |
| 3,187,431 A * | 6/1965 | Mattes | ............... | A61B 17/3213 30/339 |
| 3,906,626 A * | 9/1975 | Riuli | ................. | A61B 17/3213 30/162 |
| 4,322,885 A * | 4/1982 | Osada | ................. | B26B 5/002 30/162 |

(Continued)

*Primary Examiner* — Omar Flores Sanchez
(74) *Attorney, Agent, or Firm* — Ellenoff Grossman & Schole LLP; James M. Smedley; Alex Korona

(57) ABSTRACT

A cutting device is disclosed. The cutting device has a body member having a cavity that extends from an opening at a front end portion of the body member toward a back end portion of the body member. The cutting device also has a cutting member partially disposed in a first portion of the cavity, a first urging member portion disposed in a second portion of the cavity, and a second urging member portion disposed in a third portion of the cavity. The first portion of the cavity is disposed between the second portion and the third portion of the cavity. The cutting member is removably disposable in the first portion of the cavity between the first urging member portion and the second urging member portion.

20 Claims, 3 Drawing Sheets

(56) References Cited

U.S. PATENT DOCUMENTS

| | | | | |
|---|---|---|---|---|
| 4,660,287 A * | 4/1987 | Decker | ............... | B26B 5/00 30/162 |
| 5,417,518 A * | 5/1995 | Bierwith | ............... | B25G 3/28 37/457 |
| 5,711,079 A * | 1/1998 | Fischer | ............... | B26B 5/00 30/342 |
| 5,896,621 A * | 4/1999 | Lindgren | ............... | B25G 3/10 16/114.1 |
| 6,138,363 A * | 10/2000 | Kawashima | ............... | B26B 29/025 224/232 |
| 6,442,843 B1 * | 9/2002 | Jue | ............... | B26B 3/06 224/232 |
| 6,745,474 B1 * | 6/2004 | Huang | ............... | B26B 5/002 30/162 |
| 6,782,626 B1 * | 8/2004 | Gibbs | ............... | B25G 3/32 30/339 |
| 7,637,015 B1 * | 12/2009 | Biolchini, Jr. | ............... | B26B 5/00 30/125 |
| 8,413,339 B2 * | 4/2013 | Ranieri | ............... | B26B 5/002 30/162 |
| 9,480,495 B2 * | 11/2016 | Cote | ............... | A61B 17/3211 |
| 2004/0111895 A1 * | 6/2004 | Huang | ............... | B26B 5/002 30/162 |
| 2012/0198703 A1 * | 8/2012 | Ranieri | ............... | B26B 5/002 30/162 |

* cited by examiner

CUTTING DEVICE

RELATED APPLICATIONS

This application claims the benefit of U.S. Provisional Patent Application Ser. No. 62/482,569 filed Apr. 6, 2017, which is hereby incorporated by reference in its entirety.

FIELD OF THE INVENTION

The present invention generally relates to cutting devices. For example, at least some exemplary embodiments of the present disclosure relate to re-usable scalpels having a blade holding cavity that includes an urging member, which together with the walls of the cavity reversibly secures the blade and allows the blade to be removed and replaced.

BACKGROUND

A scalpel is a small and sharp bladed instrument commonly used for surgery, anatomical dissection, and various arts and crafts (craft knife or hobby knife). Scalpels typically have two parts, a cylindrical body (often flat), and a short blade held in a cavity in the body. Scalpels may be disposable or replaceable. A disposable scalpel is configured with a permanent blade, often for single use, after which the entire instrument may be discarded. Re-usable scalpels have removable blades, to replace the blade after single surgical use, or when the blade becomes dull. The blade may be changed manually, or by a specialized machine that removes the old blade to replace it with a new one, and that in surgical applications may safely retain the old blade. Such machines can put stress on the blade holding structure, in addition to the stress occurring in normal use. Due to inadequate, inconsistent or prematurely deteriorating holding power of the blade holding structure during use or during blade replacement, known structures to hold a blade may not provide adequate holding force. They may allow unacceptable blade movement or even allow the blade to fall out during use or during replacement, e.g. during processing in a machine that replaces the blade. The problem can be exacerbated by tolerances in production of the scalpel or the replacement blades e.g. by tolerances in the dimensions of the blade (width, height), of the body of the scalpel, or of other scalpel parts that affect the fit of the blade. A suitable blade holding structure would accommodate such tolerances and still provide sufficient and consistent holding power as well as durability during use and during blade replacement, to avoid creating potentially hazardous situations. For example, a loose blade may compromise the precision of the cut, or worse, the blade may fall out entirely during use of the scalpel or replacement of its blade.

Therefore, there is a need in the art for a re-usable cutting device that securely holds the blade and prevents it from loosening or falling out during regular use and during repeated replacements of the blade. For example, there is a need for a cutting device such as a re-usable scalpel that securely holds a replacement blade even if the blade width or height has a degree of tolerance. Further, there is a need for a cutting device such as a re-usable scalpel that is sufficiently durable to tolerate the repeated stress that blade replacement machines can put on the scalpel structure while maintaining a consistent holding power for each new blade. Still further, there is a need for such a cutting device such as a scalpel that exhibits these features when used with replacement blades that have a degree of tolerance in their width or height. The exemplary disclosed method and apparatus is directed to overcoming one or more of the shortcomings set forth above and/or other deficiencies in existing technology.

SUMMARY OF THE INVENTION

In one aspect, the present invention is directed to a cutting device. The cutting device includes a body member having a cavity that extends from an opening at a front end portion of the body member toward a back end portion of the body member. The cutting device also includes a cutting member partially disposed in a first portion of the cavity, a first urging member portion disposed in a second portion of the cavity, and a second urging member portion disposed in a third portion of the cavity. The first portion of the cavity is disposed between the second portion and the third portion of the cavity. The cutting member is removably disposable in the first portion of the cavity between the first urging member portion and the second urging member portion.

In another aspect, the present invention is directed to a cutting device. The cutting device includes a body member having a cavity that extends from an opening at a front end portion of the body member toward a back end portion of the body member. The cutting device also includes a cutting member partially disposed in a first portion of the cavity, a leaf spring having a first spring portion disposed in a second portion of the cavity, and a second spring portion disposed in a third portion of the cavity. The first portion of the cavity is disposed between the second portion and the third portion of the cavity. The cutting member is reversibly disposable in the first portion of the cavity between the first spring portion of the leaf spring and the second spring portion of the leaf spring.

DETAILED SPECIFICATION AND INDUSTRIAL APPLICABILITY

Figure 1:
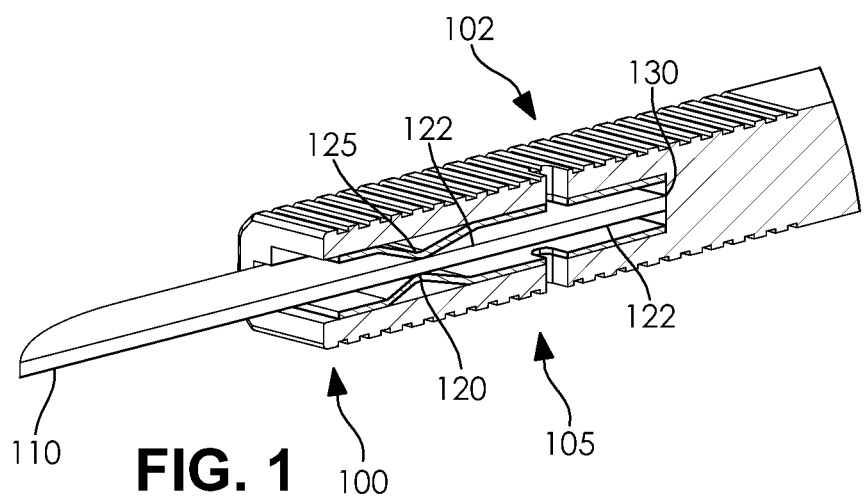
FIG. 1 is a sectional view of a long side of the cutting device in accordance with an embodiment of the present invention, showing the holding cavity for the blade.

The present invention generally relates to re-usable cutting devices such as, for example, re-usable scalpels configured to use replaceable and/or reversible blades. For example, at least some exemplary embodiments of the present invention relate to cutting devices (e.g., scalpels) having a blade holding cavity that comprises a leaf spring, which together with the walls of the cavity reversibly secures the blade and allows the blade to be removed and replaced.

FIGS. 1-6 for example illustrate a cutting device 100. Cutting device 100 may for example be a scalpel (e.g., or knife, craft knife, and/or any other suitable cutting device). In the following description of embodiments of the invention, in general, the two opposite surfaces gripped between the fingers of a user's hand holding cutting device 100 are referred to as its top and bottom (e.g., as cutting device 100 would appear if lying flat on a table). Cutting device 100 may have two distal end portions, a front end portion (e.g., front end portion 105) that holds a cutting member (e.g., blade 110), and a back end portion (e.g., back end portion 115) on the opposite side of cutting device 100 from front end portion 105. The cutting device may also have two opposite sides (left and right). In exemplary embodiments of the invention, the cutting device body (e.g., a body 102) may be of general symmetrical build, or may be configured with an ergonomical shape or surface structure, to better fit into the grip of a user's hand. Cutting device 100 may have a cover (e.g., a safety cap) 104 that may be removably attachable to front end portion 105 and/or back end portion 115.

According to at least some exemplary embodiments of the present invention, cutting device 100 may be comprised of body 102 configured with a cavity 120, blade 110 and an urging member 125. Urging member 125 may be configured to fit into cavity 120 and reversibly hold replaceable blade 110. For example, a user may removably attach blade 110 into cavity 120, and may reverse an orientation of blade 110 when inserting blade 110 in cavity 120. Cavity 120 may be open at front end portion 105, and may extend towards back end portion 115 for a distance in length sufficient to accommodate the length of the internal part (e.g., portion retained in cavity 120) of blade 110 that does not protrude from body 102. For example, the length of the internal part (e.g., portion retained in cavity 120) of blade 110 may be at least the same length as the length of the protruding external part of blade 110. For a more secure fit, the internal part of blade 110 may be 1.5, 2, 2.5, 3 or more times the length of the external part of blade 110.

According to at least some exemplary embodiments of the present invention, cavity 120 may be configured to hold blade 110 and urging member 125, with blade 110 protruding out of front end portion 105 of cutting member 100. For example as illustrated in FIG. 1, urging member 125 may not protrude from front end portion 105 (or may not protrude to a significant extent). Urging member 125 may be recessed in body 102 so that its outer edge is located inside cavity 120. The length of cavity 120 (e.g., from a top end of front end portion 105 of body 102 towards back end portion 115) may be at least the same as the length of the internal part (e.g., portion received in cavity 120) of blade 110, and may also for example be longer (for example to accommodate a weight at the opposite end of body 102 to improve balance). For example, the length of cavity 120 may be about the length of the internal part of blade 110, and the length of the external part of blade 110 may correspond to its internal part as disclosed for example herein. Also for example, the total length of body 102 from a front tip of front end portion 105 to a back tip of back end portion 115 may be from about 1 to about 10 times the length of cavity 120, or more, for example, about 2-8 times or 4-6 times the length, e.g. about 5 times the length of cavity 120.

According to at least some exemplary embodiments of the present invention, a top and/or bottom of cavity 120 may be slightly tapered towards the back of cavity 120, for example, the top and bottom walls of cavity 120 may each have a draft angle of about 0.5°-3.5°, 0.5°-2.5°, or about 1°-2°, with cavity 120 becoming for example increasingly narrow (e.g., narrower) in a direction moving toward back end portion 115. The exemplary taper may help to accommodate tolerance in the dimensions of blade 110 (e.g. width, height, or both). Also for example, side walls of cavity 120 and/or a plurality of exemplary side chambers 122 may also for example have a taper/draft angle. The taper of the side walls may be for example the same or different as disclosed above for the top and/or bottom walls of cavity 120, and the draft angle amount (e.g., amount of degrees) may be similar to the exemplary angles disclosed for example above for the top and/or bottom walls of cavity 120.

According to at least some exemplary embodiments of the present invention and as illustrated for example in FIGS. 2-4, one or more (e.g., two, three, four, or more) side chambers 122 may be configured above and below a main portion (e.g., central portion) of cavity 120 to hold urging member 125. The width of side chambers 122 may be for example smaller than the width of the main portion (e.g., central portion) of cavity 120 that holds blade 110, to improve ease of assembly and/or to better secure blade 110. Alternatively for example, the width of side chambers 122 and the width of the main portion of cavity 120 may be the same. Side chambers 122 may be tapered to a similar degree as the draft angle as the main portion of cavity 120, and for example the draft angle (e.g., amount of degrees) may be similar to those disclosed above for the top and/or bottom walls of cavity 120. Side chambers 122 may for example be symmetrical to each other to accommodate urging member 125. Also for example, side chambers 122 may be non-symmetrical, and the shape of side chambers 122 and urging member 125 may be configured and/or shaped correspondingly to provide a sufficiently tight fit upon assembly, depending on the assembly technique utilized (e.g. friction fit with or without use of adhesives, solvents or ultrasonic treatment) as described for example herein.

Urging member 125 may be for example any suitable potential-energy-storing member for urging one or more members (e.g., for urging and/or retaining blade 110) as disclosed for example herein. For example, urging member 125 may be any suitable spring such as for example a leaf spring, resilient wire or cord, an elastic member such as an elastic band (e.g., rubber band), any suitable compression member, and/or any suitable tension member. For example, urging member 125 may be a symmetrical leaf spring. Also for example, urging member 125 may include for example a number of strips of metal that may be slightly curved and clamped together. For example, urging member 125 may include a length of spring steel having a rectangular (e.g., or any suitable polygonal) cross-section. For example, urging member 125 may include one or more relatively slender arc-shaped strips of steel.

According to at least some exemplary embodiments of the present invention, urging member 125 may be flexible and made for example from metal. For example, urging member 125 may be a leaf spring that may be a one-part (e.g., "X" shape), or a two-part leaf spring. For example, urging member 125 may be a two-part leaf spring that may have a "V" or "U" shape located in an upper side chamber 122 above blade 110, and a separate part and mirror image of the "V"/"U" shape may be located in the lower side chamber 122 below blade 110. Also for example, urging member 125 may be a leaf spring that may be a one-part leaf spring, e.g., for higher holding power, durability, and/or efficiency of production. Further for example, urging member 125 may have a one-part leaf spring ("X" shape), the main portion of cavity 120 and side chambers 122 for example extending a similar distance into body 102 as blade 110. Also for example, urging member 125 may have a recess 130 (e.g., a slot) disposed near an end portion of cavity 120 located nearest to back end portion 115, recess 130 configured to accommodate a back end of blade 110.

In at least some exemplary embodiments of the present invention, urging member 125 may form a single piece, and a metal part of urging member 125 contacting a back end of the main portion (e.g., portion at which blade 110 is received) of cavity 120 may be configured with recess 130 having suitable height and width to accommodate corresponding dimensions of blade 110 (e.g., optionally accommodating tolerance in its dimensions, and optionally with a plastic or rubber insert/frame in recess 130 to accommodate tolerance but to still provide contact and stabilization for blade 110). Blade 110 may thus for example extend through some or substantially an entire thickness of urging member 125, and may be secured and stabilized by resting in recess 130. For example, blade 110 and cavity 120 may extend far enough for blade 110 to pass through recess 130 and continue for a distance, for example 0.1-10 mm, e.g., 0.2-0.5 mm (e.g., into a recess disposed in body 102). For example, recess 130 may be a slot or any other suitable type of recess.

According to at least some exemplary embodiments of the present invention, body 102 of cutting device 100 may be configured to receive cover 104 at front end portion 105 and/or back end portion 115. For example at front end portion 105, cover 104 may be configured to fit over blade 110 when not in use and may thus prevent unintended cuts and injuries. Cover 104 may be configured to also fit back end portion 115 for storage during use, in which case back end portion 115 may be configured accordingly to fit cover 104. Cover 104 may for example be rotated 180° by the user and then slid over back end portion 115 for reversible attachment. Alternatively, for example when cutting device 100 is a craft knife scalpel with a circular cylindrical body, back end portion 115 may be configured with an aperture to fit cover 104 so that distal ends of cover 104 extend out to both sides of body 102, thereby preventing rolling when cutting device 100 is placed on a surface.

According to at least some exemplary embodiments of the present invention, body 102 may be cylindrical. For example, body 102 may be flat rectangular cylindrical, for example when cutting device 100 is a surgical scalpel. For example, cutting device 100 may have two opposing pairs of surfaces substantially parallel to each other, e.g., and sides extending a few millimeters (e.g. 1-3) and a top and bottom being about 5-15 mm wide. Alternatively for example, body 102 may be circular cylindrical, elliptic cylindrical, octagonal cylindrical, or rectangular cylindrical (e.g. including a prism). Body 102 may be partially or substantially entirely hollow or solid. For example when body 102 is hollow it may include a weight, which may be located in cavity 120, or may be accommodated in a separate second cavity located at, near, and/or towards back end portion 115.

According to at least some exemplary embodiments of the present invention, body 102 and/or cover 104 may be made of one or more materials, including plastics, thermoplastics, polymers, metals, and wood.

According to at least some exemplary embodiments of the present invention, body 102 and/or cover 104 may be formed from a suitable thermoplastic material, which may include, for example, Acrylanitrile Butadiene Styrene (ABS), Polycarbonate (PC), Mix of ABS and PC, Acetal (POM), Acetate, Acrylic (PMMA), Liquid Crystal Polymer (LCP), Mylar, Polyamid-Nylon, Polyamid-Nylon 6, Polyamid-Nylon 11, Polybutylene Terephthalate (PBT), Polycarbonate (PC), Polyetherimide (PEI), Polyethylene (PE), Low Density PE (LDPE), High Density PE (HDPE), Ultra High Molecular Weight PE (UHMW PE), Polyethylene Terephthalate (PET), PolPolypropylene (PP), Polyphthalamide (PPA), Polyphenylenesulfide (PPS), Polystyrene (PS), High Impact Polystyrene (HIPS), Polysulfone (PSU), Polyurethane (PU), Polyvinyl Chloride (PVC), Chlorinated Polyvinyl chloride (CPVC), Polyvinylidenefluoride (PVDF), Styrene Acrylonitrile (SAN), Teflon TFE, Thermoplastic Elastomer (TPE), Thermoplastic Polyurethane (TPU), Engineered Thermoplastic Polyurethane (ETPU), or any combination thereof.

According to at least some exemplary embodiments of the present invention, body 102 may be made from one piece, or from multiple pieces. For example, body 102 may be configured from two pieces, e.g. two halves, which may be substantially symmetrical or non-symmetrical with regard to their outer and/or inner shape, and their outer and/or inner surface profile.

In at least some exemplary embodiments, body 102 may have two halves, each configured with one of two side chambers 122 and forming part of the main cavity 120, so that the inner shape and surface profile of the two body halves may be symmetrical. The outer shape and surface profile may be symmetrical or non-symmetrical.

According to at least some exemplary embodiments of the present invention, cutting device 100 may be assembled depending on the construction of body 102 as disclosed for example herein. For example, cutting device 100 may have urging member 125 that may be a leaf spring that may be a single metal piece, in which case urging member 125 (e.g., the leaf spring) may be inserted into cavity 120 and/or side chambers 122 by pressing the two front distal ends of urging member 125 (e.g., the leaf spring) and pushing the compressed leaf spring into cavity 120 and/or side chambers 122 until the two halves of the leaf spring rest against the side chamber walls of side chambers 122, and are held in place by the tension of the spring. Once blade 110 is inserted, additional forces may be created that press the leaf spring against the top and bottom wall of upper and lower side chambers 122, respectively. Additionally for example, an interference fit (also known as press fit or friction fit) may be used, for example for two piece leaf springs. This may include, for example, interference fits by force or temperature (thermal expansion or contraction) as described for example herein. Adhesives may also be used. In at least some exemplary embodiments, no adhesives may be used. If urging member 125 (e.g., the leaf spring) is bonded to or embedded into or otherwise attached to material of body 102 for example as illustrated in FIGS. 1-4, a portion behind the "X" shape or "V"/"U" shape (e.g., of urging member 125) may be bonded, embedded, and/or attached, and the portion towards front end portion 105 may remain free to move with changes in tension (e.g., as may occur when blade 110 is inserted or removed).

According to at least some exemplary embodiments of the present invention, body 102 may be a multiple-part piece, for example, a two-part piece. For example, body 102 may be comprised of two body halves. For example, a multiple-part body may be assembled by press fitting the leaf spring (and also for example blade 110) into cavity 120 and side chambers 122 by force (e.g., pressure), placing urging member 125 that may be a leaf spring and/or blade 110 either consecutively or at the same time. Instead of force, thermal contraction or expansion may be used to join urging member 125 and body 102. For example, adhesive may also be used. In at least some exemplary embodiments, the assembly of cutting device 100 may be achieved without use of adhesives.

According to an embodiment of the present invention, multiple pieces of body 102 (e.g. two pieces, or two halves) may be joined around urging member 125 that may be a leaf spring. To join the multiple pieces, the body parts (e.g., depending on the materials involved) may be joined using mechanical fasteners, ultrasonic welding, coatings, adhesive, or any combination thereof.

According to at least some exemplary embodiments of the present invention, a fastening element such as a hinge or latch or similar may be configured in the parts to be joined. In this case, stronger plastics may be used so that the parts remain intact during the strain of assembly. Alternatively or additionally for example, mechanical fasteners such as screws, rivets, pins, nuts, push-on lock nuts, and/or clips may be used. The mechanical fasteners may be molded in place, forced, glued and/or expanded into holes, inserted ultrasonically and/or inserted with heated probes. Mechanical fasteners may be used with suitable plastic materials that are suitably resilient to withstand the strain of fastener insertion and the stress around the fastener, depending on a shape and/or thickness of the parts. For example, if body 102 is flat and the body parts (e.g., halves) to be joined are relatively thin, a push-on lock nut or clip may for example be used (e.g., or alternatively a screw).

In at least some exemplary embodiments, the material of the body pieces to be joined may be plastics, which may be joined by ultrasonic welding, e.g. transmittal of sonic pulses to the parts by a resonant vibrating tool (e.g., a horn), which may cause two plastic materials to vibrate against each other. The vibration both heats and fuses the parts together, without use of glues or solvents. Plastic parts including those composed of blends or alloys of different resin families may be welded (e.g., if their melting temperatures are within e.g. about 30° F. and their composition is compatible).

In at least some exemplary embodiments, the material of the body pieces to be joined may be thermoplastics that are softened by coating them with a solvent, then clamping or otherwise pressing the pieces and for example urging member 125 (e.g., a leaf spring) together to bond them upon evaporation of the solvent. Optionally, elevated temperature may be used to cure the bond, and if the material of the body parts to be joined are clear materials, they may be cured (e.g., substantially instantly cured) using high-intensity ultraviolet light.

In at least some exemplary embodiments, adhesive may be used to join body pieces and urging member 125 (e.g., a leaf spring), and/or adhesive may be used in addition to any of the joining methods disclosed herein, or may be used in addition to a combination of the above-described methods.

In at least some exemplary embodiments, the assembly of a multiple-part body 102 may be achieved without adhesives and/or without solvents.

According to at least some exemplary embodiments of the present invention, body 102 may be a one part piece, and to assemble cutting device 100 from its component parts (e.g., body 102, urging member 125, and/or exchangeable blade 110), urging member 125 that may be a leaf spring may be press fit into side chambers 122 of cavity 120. Also for example, adhesive may be used. In an exemplary embodiment, assembly of body 102 and urging member 125 (e.g., and optionally blade 110) may be achieved without use of adhesives or solvents.

According to at least some exemplary embodiments of the present invention, cover 104 may be of a shape configured to fit (e.g., relatively closely fit) the contours of body 102, and may be tapered slightly. Typically, the circumference of cover 104 may match or may be slightly larger than the outer circumference of body 102 to provide a somewhat loose friction fit that may be tight enough to stay on cutting device 100, but loose enough to be pulled off of cutting device 100 easily by hand by a user. Cover 104 may match the body's geometrical shape, e.g. a flat cylindrical body that may have a flat cylindrical cap, or a circular cylindrical body that may have a circular cylindrical cap (e.g., or any other suitable configurations).

According to at least some exemplary embodiments of the present invention, blade 110 used in cutting device 100 of the present invention may be constructed from a ceramic material that is capable of withstanding extended use without becoming dull or unusable. Ceramic materials appropriate for such construction include, but are not limited to, Zirconium Oxide. One of ordinary skill in the art would appreciate that there are numerous ceramic materials that could be utilized with embodiments of the present invention. Alternatively, embodiments of the present invention may be used with standard scalpel blades, for example, a metal or steel blade. According to an embodiment of the present invention, blade 110 used in cutting device 100 may be configured with a rounded tip to reduce the chance of injury.

According to at least some exemplary embodiments of the present invention, cavity 120 may be formed depending on the method of manufacture, e.g. by additive or reductive manufacturing/machining or by configuring a mold accordingly, e.g. with a "negative" of the cavity (e.g. a protrusion), before injection molding. Body 102 may be formed with cavity 120 during manufacturing (e.g. by a suitable mold), or may be manufactured without cavity 120, and cavity 120 may then be provided after the manufacture of body 102 by taking away some of the body material with tools suitable for the material of body 102 (e.g. for cutting, broaching, milling, carving, sawing, grinding, boring, and/or drilling).

According to at least some exemplary embodiments of the present invention, cutting device 100 may be configured to retain a weight within a hollow cavity of body 102. When the weight is placed inside body 102 of cutting device 100, the weight may be secured in such a manner as to hold the weight in place, for example, a compression fit within an inner wall of body 102 (e.g., and optional adhesive). According to at least some exemplary embodiments of the present invention, the weight may be placed towards back end portion 115 of cutting device 100 (e.g., at an opposite end of cutting device 100 from blade 110), to add balance to cutting device 100, to help a user to better control the bladed end, and/or to improve the safety of using cutting device 100.

Many suitable methods and corresponding materials to make body 102 and/or cover 104 may be used. According to at least some exemplary embodiments of the present invention, cutting device 100 may be formed by 3D printing (also known as "additive" manufacturing), CNC machined parts (also known as "subtractive" manufacturing), and/or injection molding. Thermoplastic and thermosetting polymers, resins and elastomers (e.g., as disclosed for example herein) may be used. Many plastics, polymers and resins may be utilized, for example, depending on desired strength and flexibility.

Figure 2:
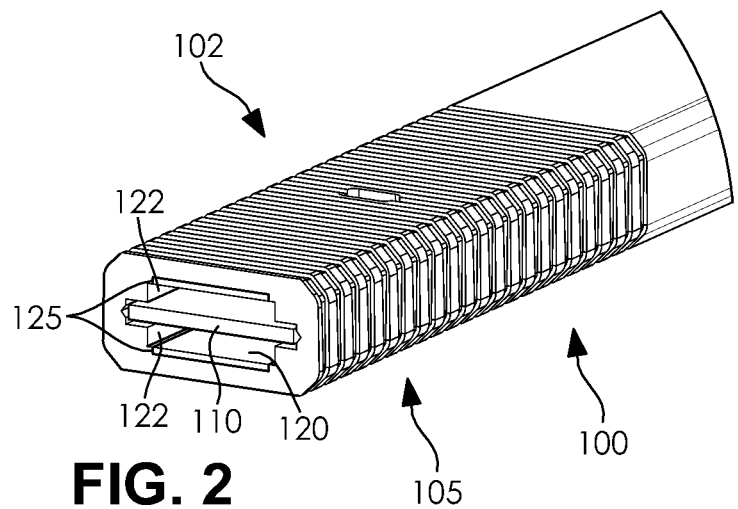
FIG. 2 is a sectional view of the short front/blade-holding side of the cutting device in accordance with an embodiment of the present invention, showing the holding cavity for the blade.
Figure 3:
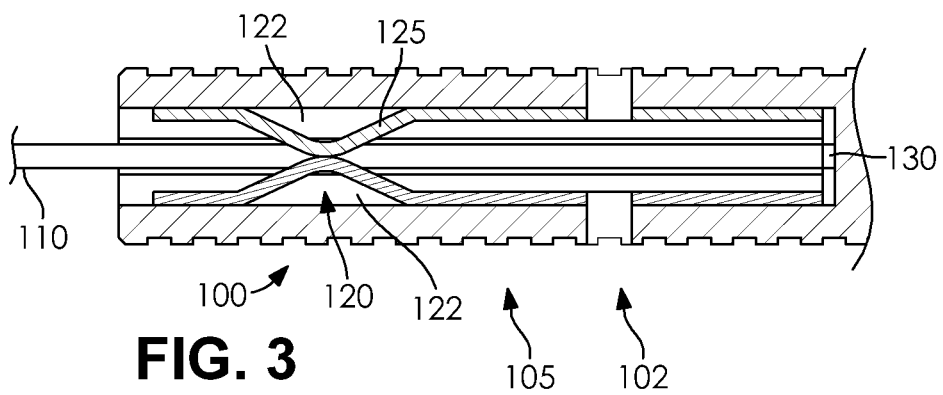
FIG. 3 is a schematic view of a cutting device in accordance with an embodiment of the present invention, showing a cross-section of the cutting device that corresponds to the surface of the cut shown in FIG. 1.

Turning to FIG. 1, a sectional view of a long side of cutting device 100 that may be for example a scalpel in accordance with at least some exemplary embodiments of the present invention is shown. In this illustration, an exemplary embodiment of the present invention is shown with its holding cavity 120 and/or side chambers 122 for blade 110 and urging member 125 that may be a one-piece leaf spring;

Turning to FIG. 2, a sectional view of the front/short blade-holding side of cutting device 100 that may be a scalpel in accordance with at least some exemplary embodiments of the present invention is shown. In this illustration, an exemplary embodiment of the present invention is shown with the holding cavity 120 and/or side chambers 122 for blade 110 and urging member 125 that may be a one-piece leaf spring;

Turning to FIG. 3, a schematic view of cutting device 100 that may be a scalpel in accordance with at least some exemplary embodiments of the present invention is shown. In this illustration, an exemplary embodiment of cutting device 100 that may be a scalpel is shown with its cross-section that corresponds to the surface of the cut shown in FIG. 1.

Figures 4, 5:
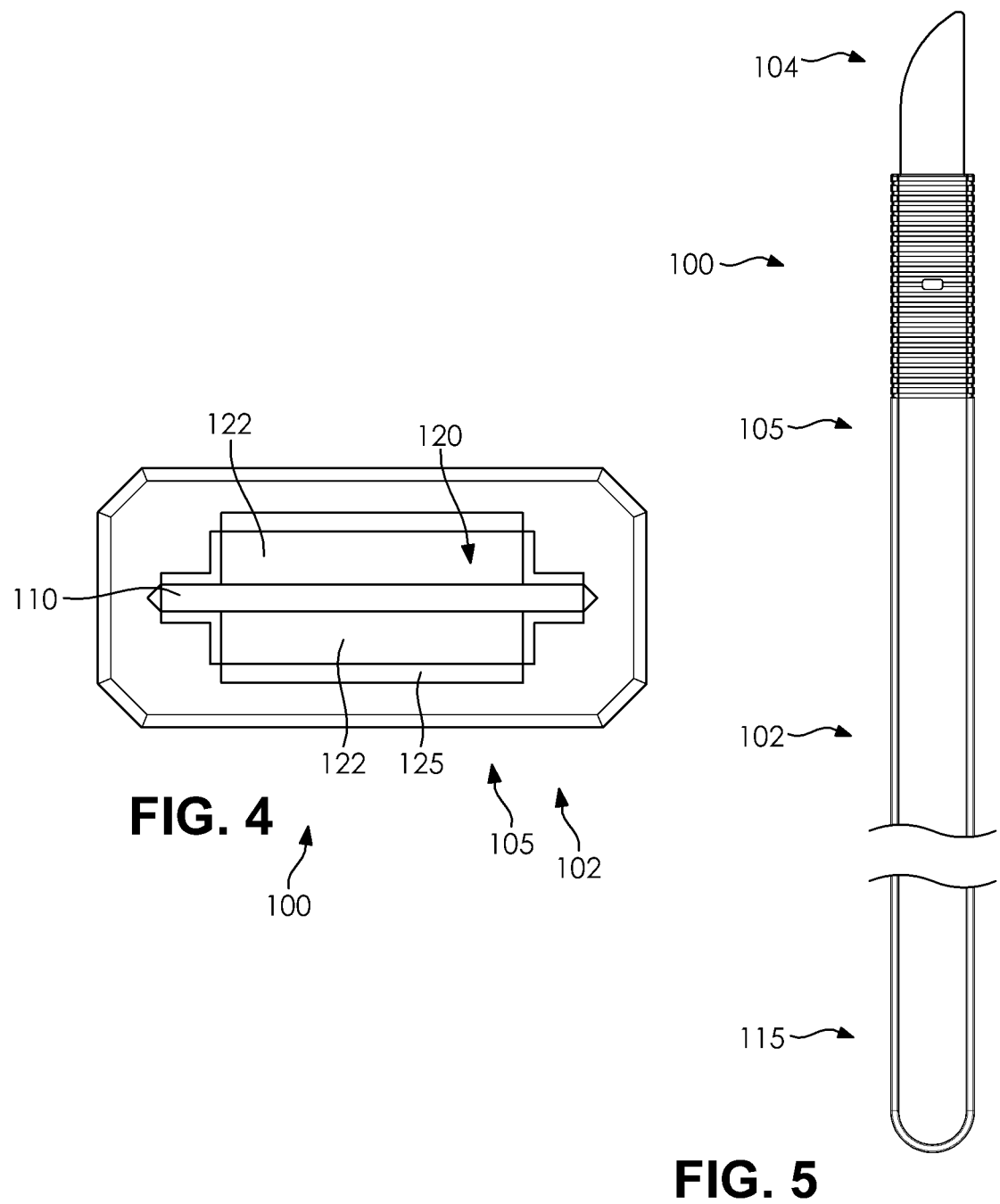
FIG. 4 is a schematic view of a cutting device in accordance with an embodiment of the present invention, showing a cross-section of the cutting device that corresponds to the surface of the cut shown in FIG. 2.
FIG. 5 is a perspective view of a cutting device in accordance with an embodiment of the present invention.

Turning to FIG. 4, a schematic view of cutting device 100 that may be a scalpel in accordance with at least some exemplary embodiments of the present invention is shown. In this illustration, an exemplary embodiment of cutting device 100 that may be a scalpel is shown with its cross-section that corresponds to the surface of the cut shown in FIG. 2, and with its two side chambers 122, one above and one below blade 110; and Turning to FIG. 5, a perspective view of cutting device 100 that may be a scalpel in accordance with at least some exemplary embodiments of the present invention is shown. In this illustration, cutting device 100 that may be a scalpel is shown with cover 104 covering front end portion 104, and the relatively wider top and relatively narrower side of cutting device 100 is illustrated.

Figure 6:
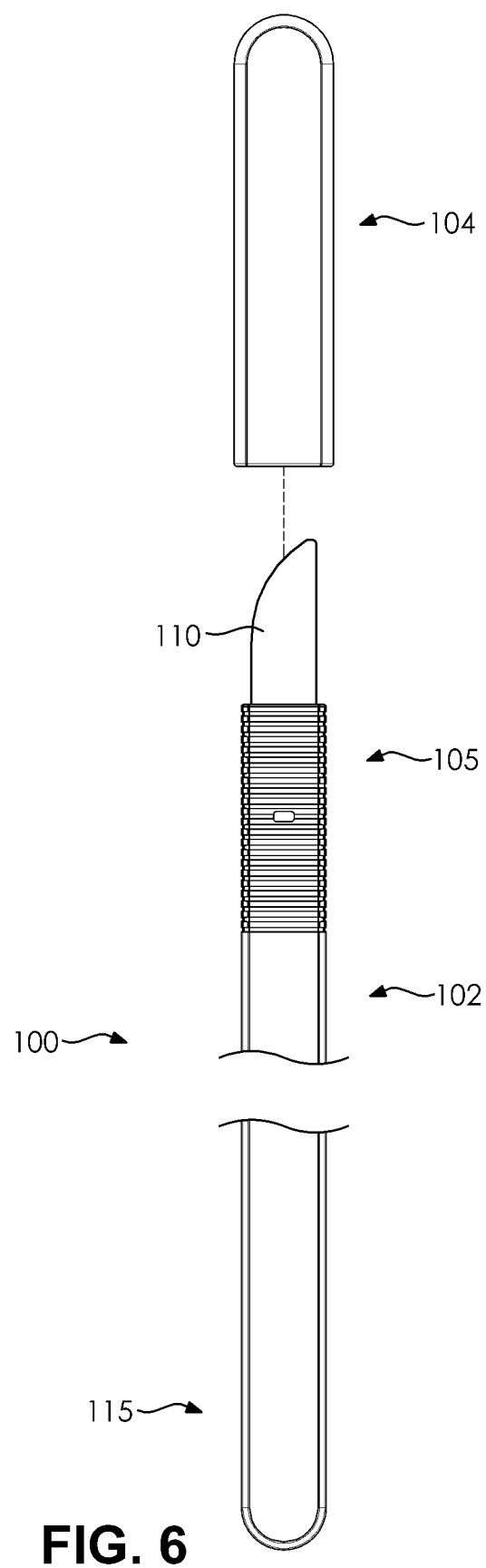
FIG. 6 is an orthogonal view of the cutting device in accordance with embodiments of the present invention, showing its top and/or bottom.

Turning to FIG. 6, an orthogonal view of cutting device 100 that may be a scalpel in accordance with at least some exemplary embodiments of the present invention is shown. In this illustration, the top (or bottom) of cutting device 100 is shown, as well as cover 104 (e.g., shown as detached) and blade 110 that may be rounded.

In at least some exemplary embodiments, an exemplary cutting device (e.g., cutting device 100) may have a body member (e.g., body 102) having a cavity (e.g., cavity 120) that extends from an opening at a front end portion (e.g., front end portion 105) of the body member toward a back end portion (e.g., back end portion 115) of the body member. The cutting device may also have a cutting member (e.g., blade 110) partially disposed in a first portion of the cavity, a first urging member portion (e.g., portion of urging member 125) disposed in a second portion (e.g., side chamber 122) of the cavity, and a second urging member portion (e.g., portion of urging member 125) disposed in a third portion (e.g., side chamber 122) of the cavity. The first portion of the cavity may be disposed between the second portion and the third portion of the cavity. The cutting member may be removably disposable in the first portion of the cavity between the first urging member portion and the second urging member portion. The first urging member portion and the second urging member portion may be for example portions of a leaf spring, which may be an X-shaped leaf spring. The leaf spring may include for example a recess (e.g., recess 130) configured to receive a back end portion of the cutting member when the cutting member is disposed in the first portion of the cavity. The cutting member may be reversibly disposable in the first portion of the cavity. The cutting device may be for example a surgical scalpel. A width of the first portion of the cavity may be for example greater than a width of the second portion of the cavity and a width of the third portion of the cavity. Also for example, an inserted length of the cutting member that is disposed in the cavity may be greater than or equal to an exposed length of the cutting member that protrudes from the cavity.

In at least some exemplary embodiments, an exemplary cutting device (e.g., cutting device 100) may have a body member (e.g., body 102) having a cavity (e.g., cavity 120) that extends from an opening at a front end portion (e.g., front end portion 105) of the body member toward a back end portion (e.g., back end portion 115) of the body member. The cutting device may also have a cutting member (e.g., blade 110) partially disposed in a first portion of the cavity, a leaf spring having a first spring portion (e.g., portion of urging member 125) disposed in a second portion (e.g., side chamber 122) of the cavity, and a second spring portion (e.g., portion of urging member 125) disposed in a third portion (e.g., side chamber 122) of the cavity. The first portion of the cavity may be disposed between the second portion and the third portion of the cavity. The cutting member may be removably disposable in the first portion of the cavity between the first spring portion of the leaf spring and the second spring portion of the leaf spring. The first spring portion and the second spring portion may for example urge against the cutting member when the cutting member is disposed in the first portion of the cavity. A width of the cutting member may for example be greater than a width of the first spring portion and a width of the second spring portion. The cutting member may for example be formed from Zirconium Oxide. A weight for example may be disposed at the back end portion of the cutting member. The cutting device may for example include a cover that is removably attachable to the front end portion and the back end portion of the cutting device. The cutting device may for example be a scalpel. The cutting member may for example be a replaceable blade. Also for example, a total length of the body member may be, e.g., between about 4 times and about 6 times of a length of the cavity.

The exemplary disclosed apparatus and method may be used in any suitable application for utilizing a cutting device. For example, the exemplary disclosed apparatus and method may be used in any suitable technique for providing and/or using a cutting device having a replaceable and/or reversible blade. For example, the exemplary disclosed apparatus and method may be used in any suitable application for providing and using a scalpel having a replaceable and/or reversible blade.

The exemplary disclosed apparatus and method may provide a cutting device that may be used safely and efficiently. For example, the exemplary disclosed apparatus and method that may securely hold a blade in place and prevent it from loosening or falling out during regular use and/or during repeated replacements of the blade. For example, the exemplary disclosed apparatus and method may securely hold a replacement blade in place even if the blade width or height has a degree of tolerance. Further for example, the exemplary disclosed apparatus and method may provide an effective technique for providing a cutting device having a replaceable and/or reversible blade such as, e.g., a scalpel. Further for example, the exemplary disclosed apparatus and method may provide a re-usable cutting device that is sufficiently durable to tolerate the repeated stress that blade replacement machines can put on the cutting device structure while maintaining a consistent holding power for each new blade.

It should be noted that the features illustrated in the drawings are not necessarily drawn to scale, and features of one embodiment may be employed with other embodiments as the skilled artisan would recognize, even if not explicitly stated herein. Descriptions of well-known components and processing techniques may be omitted so as to not unnecessarily obscure the embodiments.

While multiple embodiments are disclosed, still other embodiments of the present invention will become apparent to those skilled in the art from this detailed description. The invention is capable of myriad modifications in various obvious aspects, all without departing from the spirit and scope of the present invention. Accordingly, the drawings and descriptions are to be regarded as illustrative in nature rather than restrictive.

What is claimed is:

1. A cutting device, comprising:
   a body member having a cavity that extends from an opening at a front end portion of the body member toward a back end portion of the body member;
   a cutting member partially disposed in a first portion of the cavity; and
   a first urging member portion disposed in a second portion of the cavity and a second urging member portion disposed in a third portion of the cavity;
   wherein the first portion of the cavity is disposed between the second portion and the third portion of the cavity;
   wherein the cutting member is removably disposable in the first portion of the cavity between the first urging member portion and the second urging member portion;
   wherein the first urging member portion and the second urging member portion are portions of a leaf spring; and
   wherein the leaf spring includes a recess configured to receive a back end portion of the cutting member when the cutting member is disposed in the first portion of the cavity.

2. The cutting device of claim 1, wherein the leaf spring is an X-shaped leaf spring.

3. The cutting device of claim 1, wherein the cutting member is reversibly disposable in the first portion of the cavity.

4. The cutting device of claim 1, wherein the cutting device is a surgical scalpel.

5. The cutting device of claim 1, wherein a width of the first portion of the cavity is greater than a width of the second portion of the cavity and a width of the third portion of the cavity.

6. The cutting device of claim 1, wherein an inserted length of the cutting member that is disposed in the cavity is greater than or equal to an exposed length of the cutting member that protrudes from the cavity.

7. A cutting device, comprising:
   a body member having a cavity that extends from an opening at a front end portion of the body member toward a back end portion of the body member;
   a cutting member partially disposed in a first portion of the cavity; and
   a first urging member portion disposed in a second portion of the cavity and a second urging member portion disposed in a third portion of the cavity;
   wherein the first portion of the cavity is disposed between the second portion and the third portion of the cavity;
   wherein the cutting member is reversibly disposable in the first portion of the cavity between the first urging member portion and the second urging member portion;
   wherein the first urging member portion urges against a first surface of the cutting member when the cutting member is disposed in the first portion of the cavity; and
   wherein the second urging member portion urges against a second surface of the cutting member, the second surface being disposed at an opposite side of the cutting member from the first surface, when the cutting member is disposed in the first portion of the cavity.

8. The cutting device of claim 7, wherein a width of the cutting member is greater than a width of the first urging member portion and a width of the second urging member portion.

9. The cutting device of claim 7, wherein the cutting member is formed from Zirconium Oxide.

10. The cutting device of claim 7, further comprising a weight disposed at the back end portion.

11. The cutting device of claim 7, further comprising a cover that is removably attachable to the front end portion and the back end portion.

12. The cutting device of claim 7, wherein the cutting device is a scalpel.

13. The cutting device of claim 7, wherein the cutting member is a replaceable blade.

14. A cutting device, comprising:
    a body member having a cavity that extends from an opening at a front end portion of the body member toward a back end portion of the body member;
    a replaceable blade partially disposed in a first portion of the cavity; and
    a spring having a first spring portion disposed in a second portion of the cavity and a second spring portion disposed in a third portion of the cavity;
    wherein the first portion of the cavity is disposed between the second portion and the third portion of the cavity;
    wherein the replaceable blade is removably disposable in the first portion of the cavity between the first spring portion of the spring and the second spring portion of the spring; and
    wherein the spring includes a recess configured to receive a back end portion of the replaceable blade when the replaceable blade is disposed in the first portion of the cavity.

15. The cutting device of claim 14, wherein a total length of the body member is between about 4 times and about 6 times of a length of the cavity.

16. The cutting device of claim 14, wherein the spring is a leaf spring and the cutting device is a scalpel.

17. The cutting device of claim 16, wherein the replaceable blade is reversibly disposable in the first portion of the cavity.

18. The cutting device of claim 7, wherein each of the first urging member portion and the second urging member portion includes one or more arc-shaped strips of steel.

19. The cutting device of claim 7, wherein the first urging member portion and the second urging member portion form a two-part leaf spring.

20. The cutting device of claim 7, wherein each of the first urging member portion and the second urging member portion includes a plurality of strips of metal that are curved and attached together.

* * * * *